(12) United States Patent
Wondrak et al.

(10) Patent No.: US 7,226,937 B2
(45) Date of Patent: Jun. 5, 2007

(54) METHODS FOR MODULATING PHOTOTOXICITY

(75) Inventors: Georg T. Wondrak, Tucson, AZ (US);
Michael J. Roberts, Tucson, AZ (US);
Moonsun Kim, Tucson, AZ (US);
Myron K. Jacobson, Tucson, AZ (US);
Elaine L. Jacobson, Tucson, AZ (US)

(73) Assignee: Board of Regents on Behalf of the University of Arizona, Tucson, AZ (US)

( * ) Notice: Subject to any disclaimer, the term of this patent is extended or adjusted under 35 U.S.C. 154(b) by 37 days.

(21) Appl. No.: 11/226,615

(22) Filed: Sep. 13, 2005

(65) Prior Publication Data

US 2006/0009416 A1  Jan. 12, 2006

Related U.S. Application Data

(62) Division of application No. 10/418,629, filed on Apr. 17, 2003, now Pat. No. 6,992,071.

(60) Provisional application No. 60/374,033, filed on Apr. 19, 2002.

(51) Int. Cl.
*A61K 31/44* (2006.01)

(52) U.S. Cl. .................. 514/354; 514/356; 514/345
(58) Field of Classification Search ................ 514/354, 514/356, 345
See application file for complete search history.

(56) References Cited

U.S. PATENT DOCUMENTS

| | | | |
|---|---|---|---|
| 5,681,554 A * | 10/1997 | Cannell et al. | 424/70.14 |
| 6,013,250 A * | 1/2000 | Cannell et al. | 424/70.51 |
| 6,225,306 B1* | 5/2001 | Ohtake et al. | 514/211.08 |
| 6,318,023 B1* | 11/2001 | Yamashita | 504/117 |
| 6,464,992 B2* | 10/2002 | Jacobson et al. | 424/401 |
| 6,992,071 B2* | 1/2006 | Wondrak et al. | 514/45 |
| 2001/0056085 A1* | 12/2001 | Ramu | 514/154 |
| 2002/0006394 A1* | 1/2002 | Redmond et al. | 424/93.7 |
| 2002/0006418 A1* | 1/2002 | Kung et al. | 424/401 |
| 2002/0064560 A1* | 5/2002 | Kung et al. | 424/487 |

FOREIGN PATENT DOCUMENTS

| | | | |
|---|---|---|---|
| WO | WO2003/088909 | * | 10/2003 |
| WO | WO2006/042625 | * | 4/2006 |

* cited by examiner

*Primary Examiner*—Vickie Kim
(74) *Attorney, Agent, or Firm*—Fulbright & Jaworski LLP

(57) ABSTRACT

The invention relates to methods for modulating photodamage via the use of collagen derived molecules which either enhance or inhibit damage caused by ultraviolet light.

7 Claims, 13 Drawing Sheets

Cytotoxic effects of the combined action of sensitizer and irradiation were assessed by comparing cell viability two days after treatment with viability of mock-treated controls. Viability was quantified using the MTS-reduction assay performed on 96-well microtiter plates. Panel A: 30 minUVA: 9.9 J/cm²; panel B: 100 µM NE-3HP Apoptotic effects of the combined action of sensitizer and irradiation were assessed by annexin V - propidium iodide (PI) staining followed by flowcytometry.

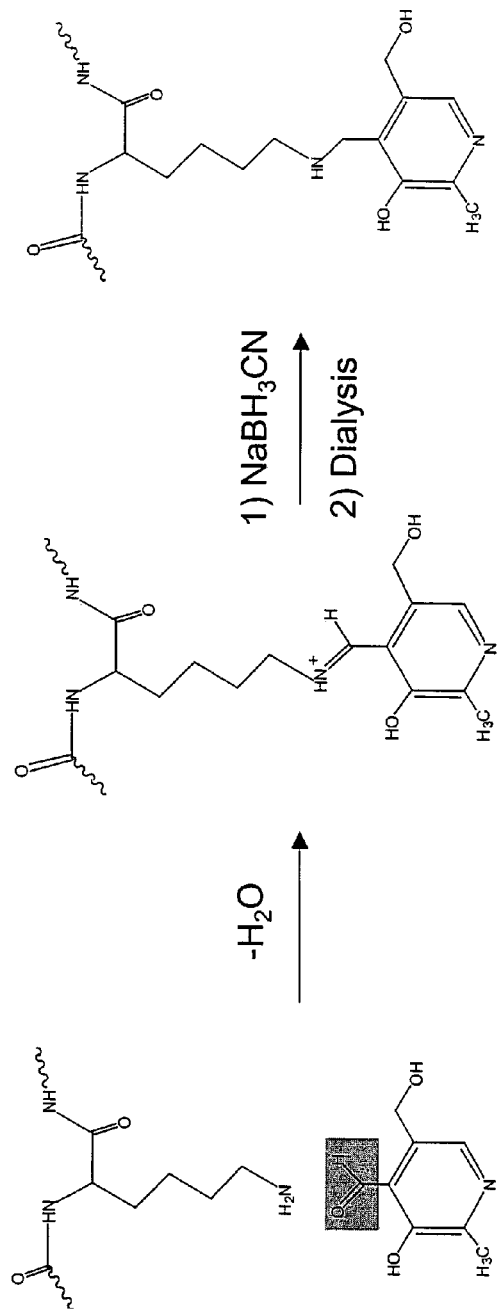

Reductive Coupling of Pyridoxal [Vitamin B6-aldehyde] to Bovine Serum Albumin [BSA] as an Example of Photodynamic Activation of a Selected Protein or Peptide A lysine-side chain of albumin is covalently modified by reaction with a small sensitizer aldehyde pyridoxal. The initially formed Schiff base is specifically reduced using NaCNBH$_3$ in water. After extensive dialysis, the protein-adduct, called BSA-B6 is characterized by mass spectrometry and fluorescence spectroscopy. The initial incubation for BSA-B6 synthesis contains: BSA [350 mg], NaCNBH$_3$ [58 mg], pyridoxal [64 mg] in a total volume of 1.5 mL 0.25 M phosphate buffer, pH 7.4. The reaction proceeds at 37 °C in the dark overnight. The reaction is terminated by extensive dialysis against water at 4°C for 48 hours under light exclusion. After lyophilization the protein is ready for photodynamic action.

FIGURE 7

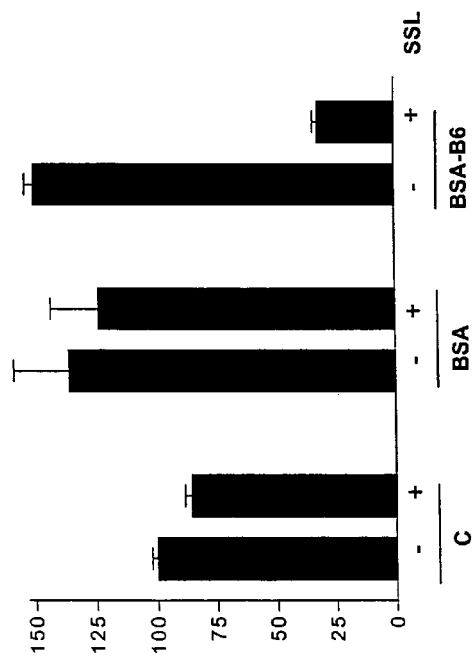

FIGURE 8

Antiproliferative effects of the combined action of BSA-B6-sensitizer and SSL irradiation were assessed by comparing cell proliferation three days after treatment with proliferation of cells treated with albumin reacted with NaCNBH$_3$ in the absence of pyridoxal [BSA]. Proliferation was quantified by cell counting using a Coulter Counter.

BSA and BSA-B6: 10 mg/mM

SSL: 2.3 J/cm$^2$ UVA + 0.12 J/cm2 UVB

C: cells +/- irradiation without protein

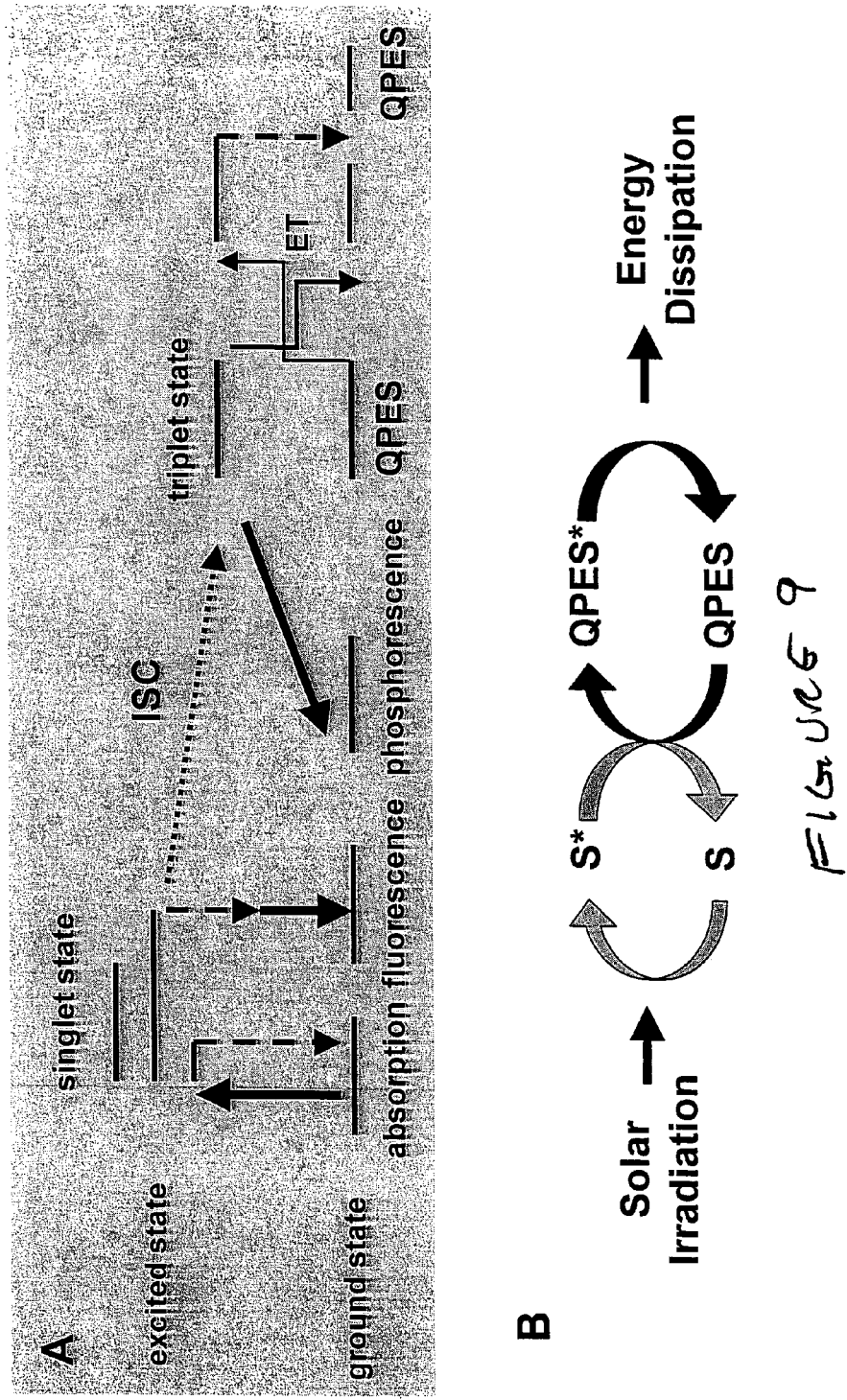

Proline and Derivatives to be protected as quenchers
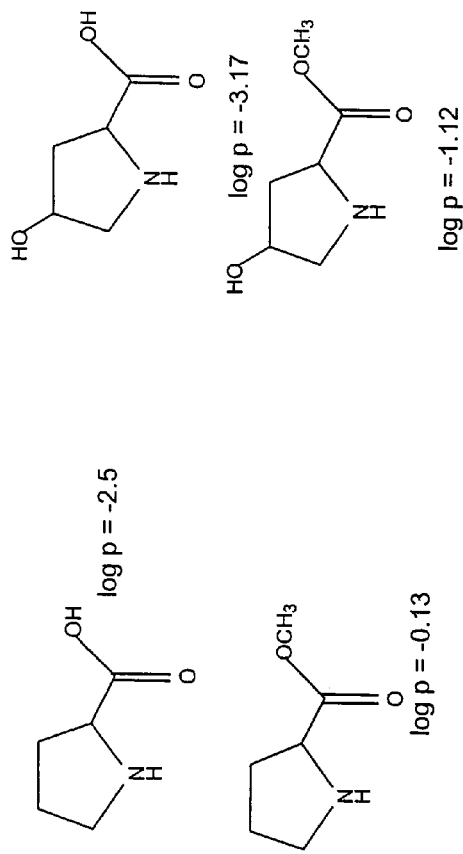
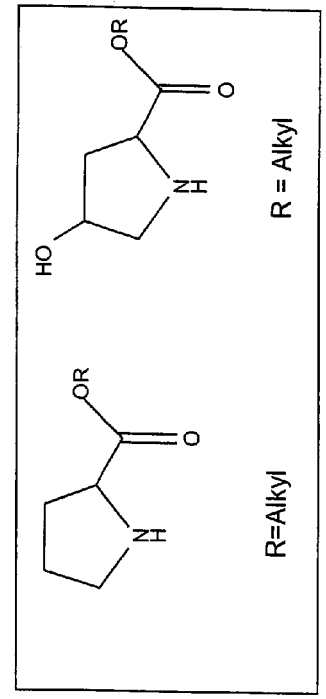
FIGURE 10

L-Pro-OCH$_3$ and 4-OH-L-Pro-OCH$_3$ are Superior QPES for the Protection of Human Skin Cells against Sensitized Photodamage not Achievable with L-Pro or 4-OH-L-Pro

US 7,226,937 B2

METHODS FOR MODULATING PHOTOTOXICITY

RELATED APPLICATIONS

This application is a divisional of Ser. No. 10/418,629, filed Apr. 17, 2003 now U.S. Pat. No. 6,992,071 incorporated by reference, and claims priority of provisional application 60/374,033, filed Apr. 19, 2002. The entire disclosure of this application is incorporated by reference herein.

FIELD OF THE INVENTION

This invention relates to molecules and compositions which are useful as modulators of skin cell phototoxicity. Specifically, "modulators" as used herein refers to materials which can either accelerate or retard the damage of cells, such as skin cells, caused by exposure to light.

BACKGROUND AND PRIOR ART

It is well known that light, UVA light in particular, is damaging to skin cells. Phototoxic cell damage occurs via the reaction of light with certain compounds that are endogenous to skin. The mechanism by which the photodamage occurs is well understood, and can be described, briefly, as follows. The molecules involved, which may be referred to as sensitizers or even accelerators of skin damage, react with light and, in the presence of oxygen, result in the formation of "reactive oxygen species", or "ROS." It is these molecules, i.e., ROS molecules, which are involved in pathways leading to cell damage, including carcinogenesis and photoaging, but not being limited to these phenomena. More details of this phenomenon may be found in Wondrak, et al. J. Invest. Dermatol 119:489-498 (2002), the entirety of which is incorporated by reference.

The fact that molecules endogenous to, e.g., the skin, are involved in accelerated phototoxicity suggests targeted therapy. To elaborate, if a compound is essentially inert in the absence of light but is involved in cellular destruction upon contact with light, then such compounds could be used in situations where targeted cell death is desired. Such situations include, but are not limited to, psoriasis, acne, premalignant and malignant hyperproliferative disorders such as actinic keratosis, and other conditions well known to the art.

Conversely, the existence of the photoactivable molecules suggests the existence of molecules which act to quench or to inhibit the effect of light on cells. Such quenchers or inhibitors can be used in situations where the harmful effects of light need to be reversed, and/or inhibited. Such quenchers or inhibitors may be used prophylactically, as well as therapeutically.

Hence, the modulation of phototoxicity on cells is the focus of the invention described herein, as will be seen in the disclosure which follows. Modulators, as used herein, refers to molecules which may be derived from skin components, collagen in particular.

BRIEF DESCRIPTION OF THE FIGURES

FIG. 7 presents schematically the synthesis of BSA-B6 complexes.

FIG. 8 shows that the complexes of FIG. 7 were effective in inhibiting cell proliferation.

FIG. 9 is a proposed mechanism for the quenching of photoactivated molecules by energy transfer ("ET" in the figure). "S*" is the fully excited sensitizer, while "S" is the sensitizer.

FIG. 10 sets forth structures of proline derivatives tested as quenchers.

DETAILED DESCRIPTION OF PREFERRED EMBODIMENTS

EXAMPLE 1

Components of the endogenous skin component, to collagen were believed to be most likely the causative agents of phototoxic damage and/or inhibition thereof. Hence, such molecules were investigated.

Figure 1:
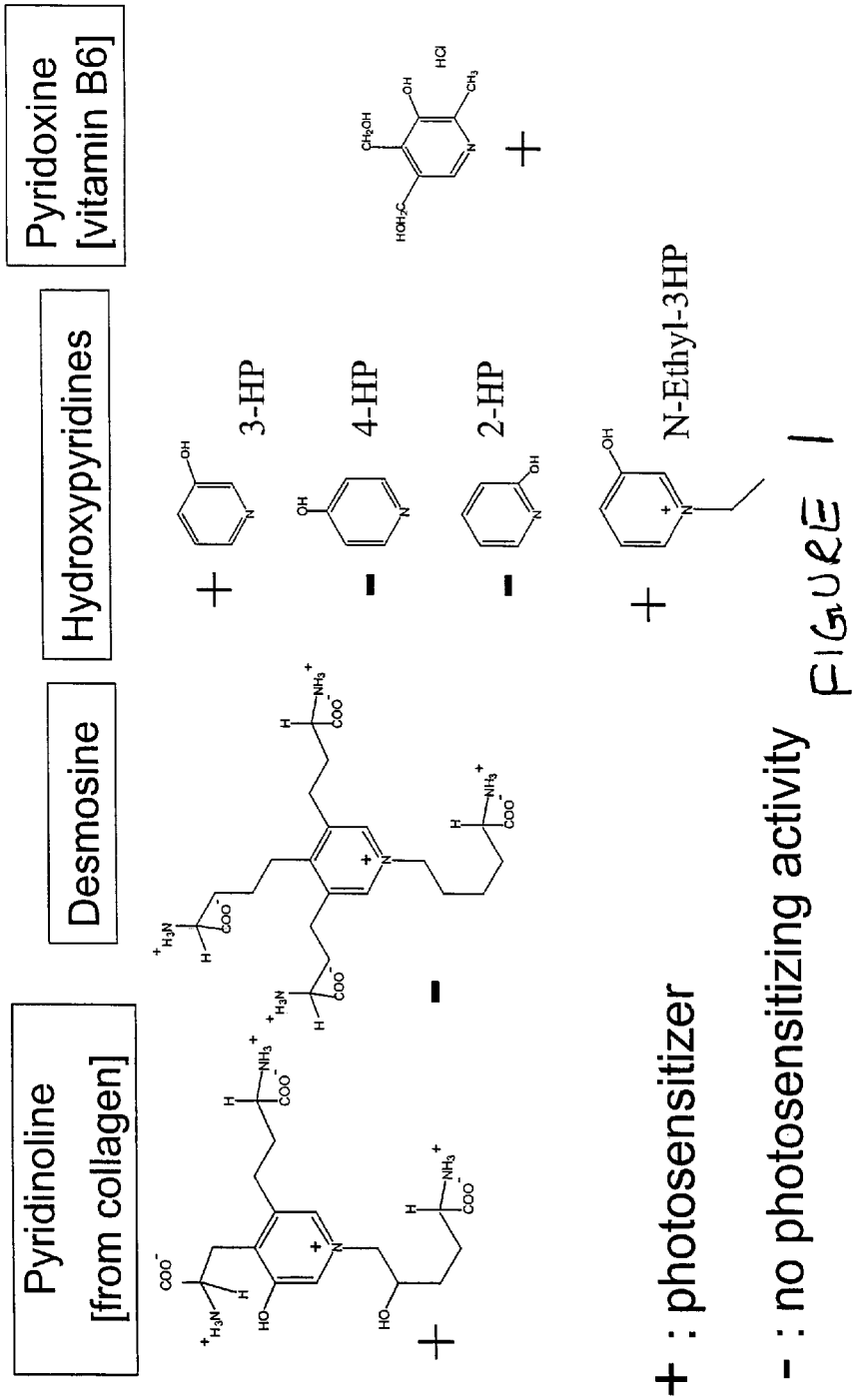
FIG. 1 sets forth the structures of various molecules employed in the examples.

Pyridinoline is an amino acid involved in cross linking collagen molecules, and it was investigated for its role in phototoxicity. The structure of pyridinoline is well known, and is depicted in FIG. 1, together with the structure of other molecules described herein.

Figure 2:
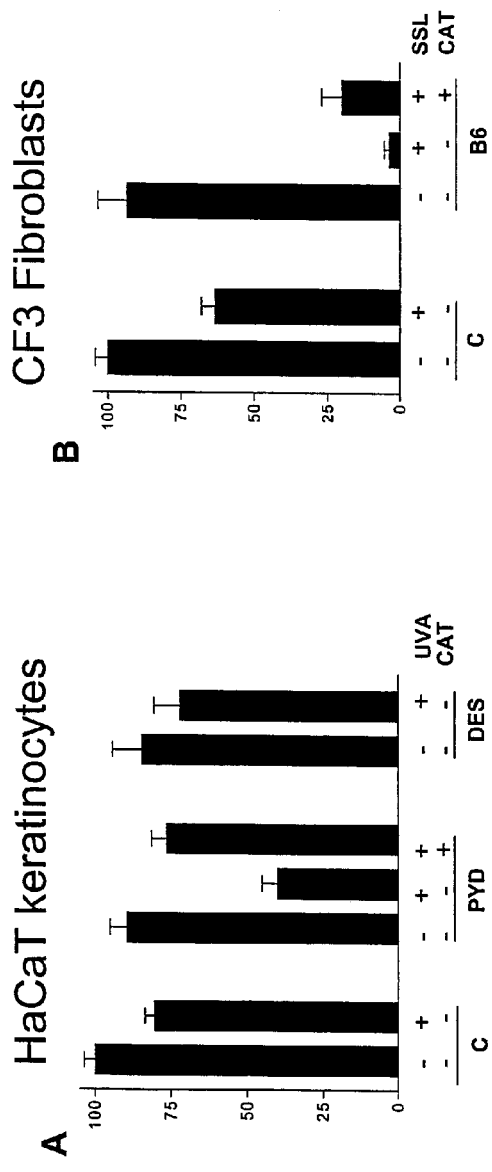
FIG. 2 depicts results showing that molecules with a 3 hydroxypyridine central structure were efficacious in provoking inhibition of cell proliferation, when exposed to light.

A series of experiments were carried out on HaCaT keratinocytes, and human CF3 fibroblasts. In these experiments, cell samples were contacted with 500 µM of pyridinoline, 500 µM of desmosine, which is an elastin constituent with a structure related to pyridinoline, or 500 µM of vitamin B6 (pyridoxine). Controls received no added compound. In one set of experiments, the cells received no external light source. In another set of experiments, they received UVA light, at 3.3 J/cm$^2$. The CF3 fibroblasts received solar simulated light, or "SSL," which combines 2.3 J/cm$^2$ of UVA light, and 0.12 J/cm$^2$ of UVB light. Results are shown, in FIG. 2, in terms of percent of cell proliferation relative to a control (no added compound, no light). The measurements were taken 3 days after stimulation.

The results indicated that pyridinoline had an antiproliferative effect, but only in the presence of light. Vitamin B6 showed dramatically more efficacy in inhibiting the cellular proliferation.

A second set of experiments were carried out in which catalase, which is a peroxide scavenger, was added, at 400 µ/ml. The catalase had absolutely no effect on vitamin B6 sensitization, suggesting that a mechanism other than peroxide formation was involved for this molecule.

Based upon these results, structures of the compounds were compared to determine if a common structural feature of the molecules, or a "pharmacophore" could be identified. It was noted that both vitamin B6 and pyridinoline share a 3-hydroxypyridine central structure, which in turn suggested the next series of experiments.

EXAMPLE 2

A group of hydroxypyridine derivatives were studied, in experiments paralleling those described supra. In brief, 2, 3, and 4-hydroxypyridine were tested, as was N-ethyl-3-hydroxypyridine. All structures are set forth in FIG. 1.

HaCaT cells, as described supra, were tested in a proliferation inhibition assay. Cell samples received equal amounts of one of the 4 compounds listed supra and were contacted with or without either solar simulated light ("SSL") as described, supra, or UVA light alone, also as described supra.

Figure 3:
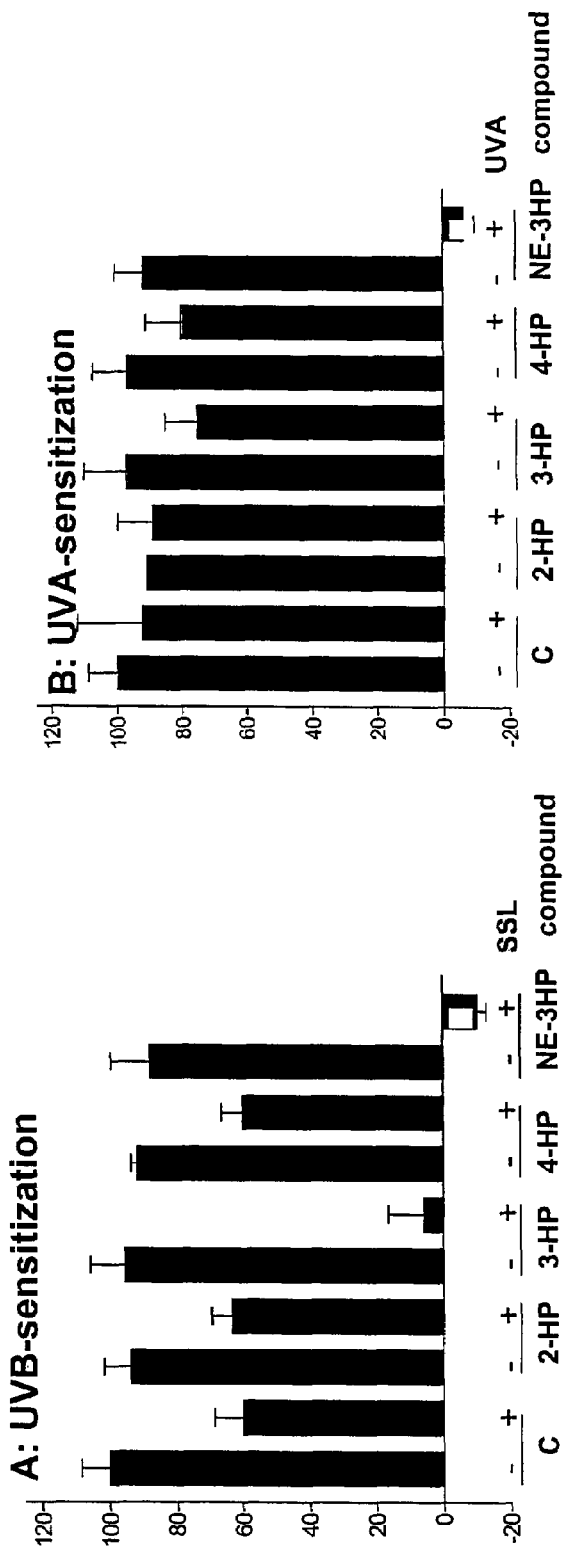
FIG. 3 compares the results obtained for the 3-hydroxypyridine compounds of FIG. 1, on HaCaT cells, which are keratinocytes, in the presence of light.

The results are depicted in FIG. 3.

As compared to controls, 3-hydroxypyridine had an inhibitory effect, where the N-ethyl derivative had a killing effect. The N-ethyl derivative also functioned in the presence of both UVA and UVB light, whereas 3-hydroxypyridine functioned in the presence of UVB light as a cell proliferation inhibitor.

EXAMPLE 3

The experiments described supra were followed by additional experiments using malignant melanoma cells (G-361 cells), and malignant breast cancer cells (MCF-7). In these experiments, the N-ethyl derivative described supra was tested as described, at varying concentrations, with UVA light at 9.9 J/cm². Viability was measured two days following the treatment. As controls, experiments were run using only the N-ethyl derivative, and only the UVA light.

Figure 4:
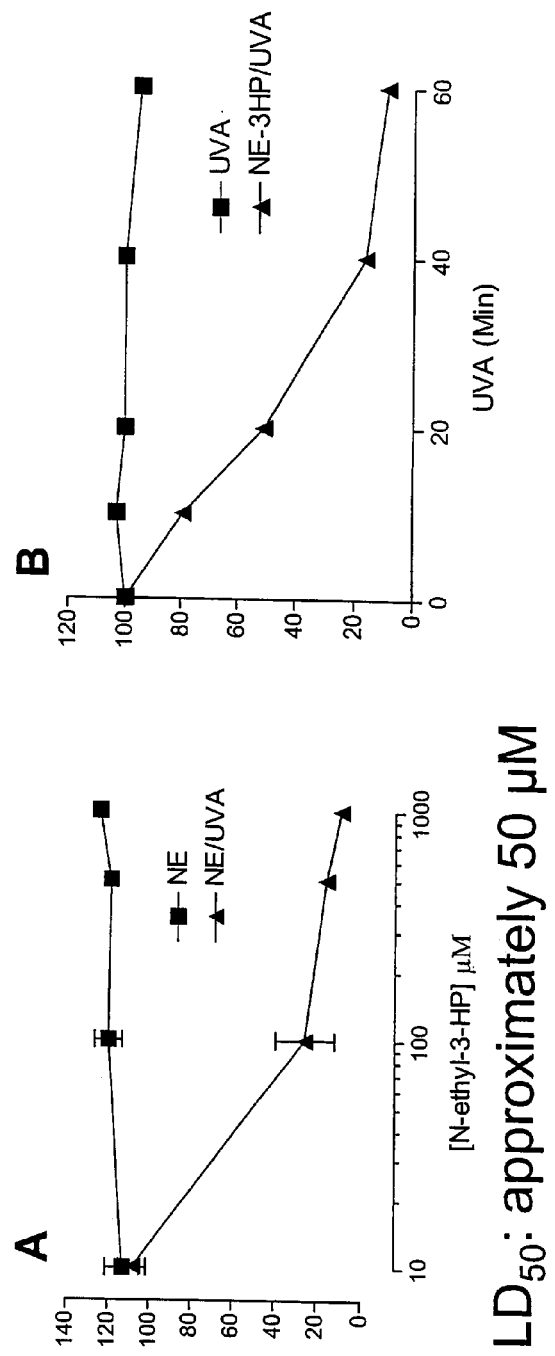
FIG. 4 depicts result obtained on malignant melanoma, using the N-ethyl derivative described herein.
Figure 5:
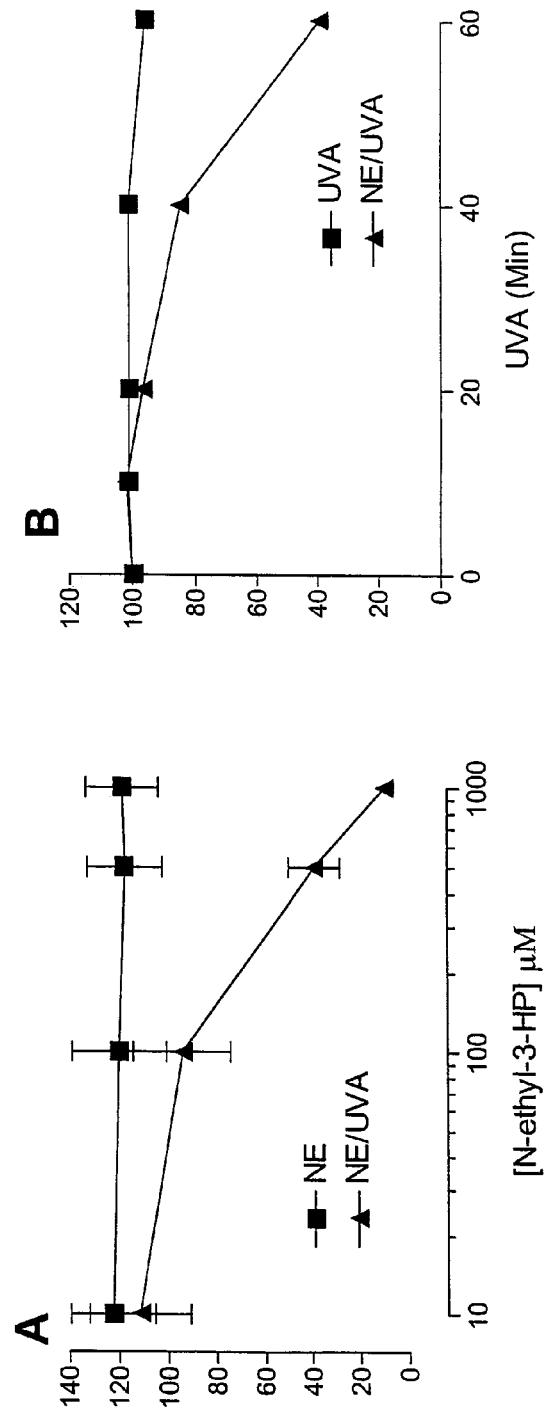
FIG. 5 parallels FIG. 4, but the cells used were breast cancer cells.

The results, shown in FIGS. 4 (G-361 cells) and 5 (MCF7 cells), show that the combination led to pronounced cytotoxicity.

Figure 6:
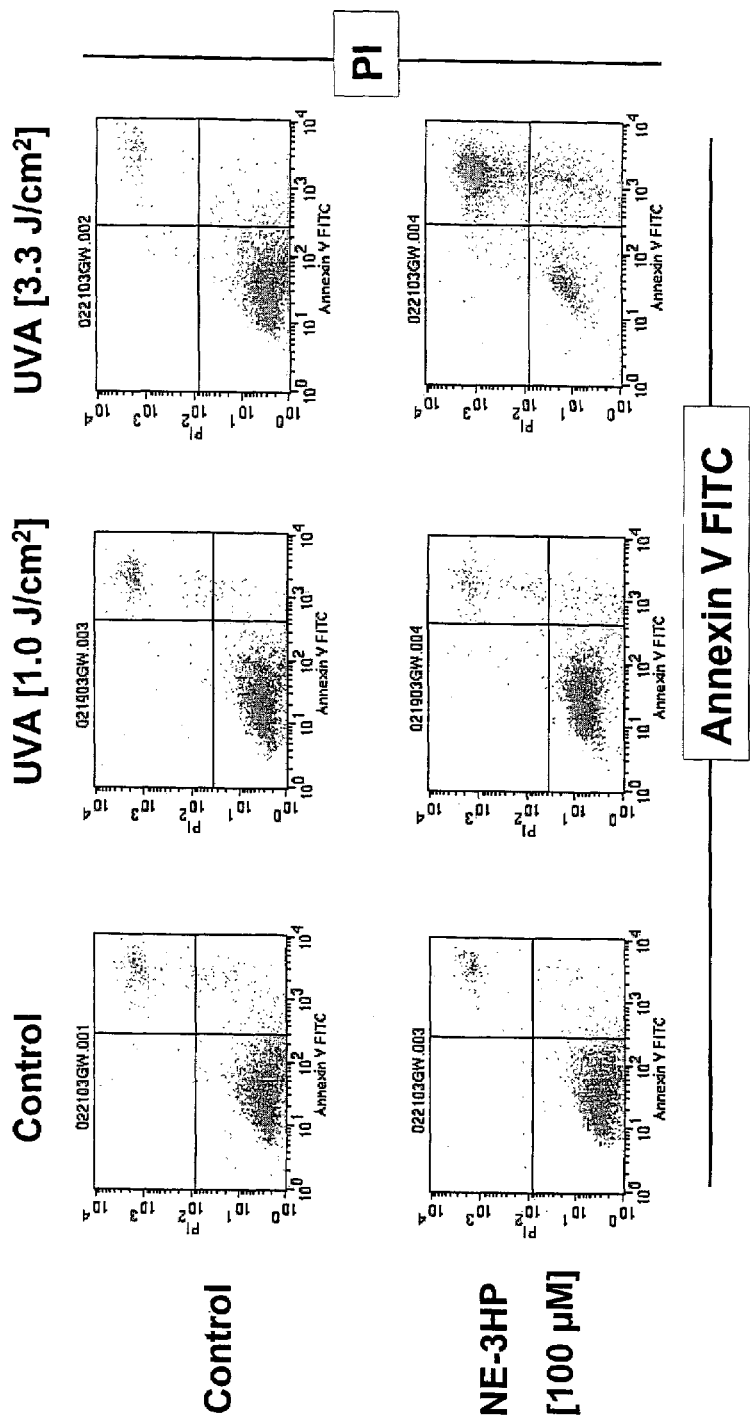
FIG. 6 presents, via FACS (flow cytometric) analysis, evidence that the N-ethyl derivative pushes cells into apoptosis.

When the G-361 cells were analyzed via FACS, the data showed that the cells were driven into programmed cell death, i.e., apoptosis. This is seen in FIG. 6, where staining with the apoptic markers annexin V and propidium iodide showed a sharp increase in stained cells when the N-ethyl derivative was used, especially with UVA at a concentration of 3.3 J/m².

EXAMPLE 4

The effective materials of the invention are small molecules. While small molecules are useful, it is sometimes desirable to complex such molecules to larger molecules, such as proteins. This facilitates targeting of the small molecule if it is complexed with, e.g., an antibody specific for a particular marker on cells, a ligand for a particular receptor, a nuclear associated protein and so forth.

To test the feasibility of this approach, vitamin B6 molecules were coupled to bovine serum albumin. In brief, a lysine side chain of the bovine serum albumin (BSA) molecule was covalently modified by reacting 350 mg of it with vitamin B6, which is a pyridoxal aldehyde (64 mg), to form a Schiff base. In turn, the Schiff base was reduced with NaCNBH₃ (58 mg) in 1.5 ml of 0.25 M phosphate buffer (pH 7.4), overnight at 37° C., and dialyzed extensively (48 hours, 4° C.). The resulting BSA-B6 adduct was characterized by mass spectrometry and fluorescence spectroscopy. The protein was then lyophilized, and used in the examples which follow. FIG. 7 depicts the synthesis. The spectroscopy work indicated that, on average, each BSA molecule was complexed to 5-6 pyroxidal molecules.

EXAMPLE 5

The antiproliferative effect of the complexes described in example 4 were tested, by adding either nothing (control), BSA, or the BSA-B6 complexes, and treating or not treating samples of HaCaT keratinocytes with SSL. The BSA and BSA-B6 were added at 10 mg/ml, and the SSL was 2.3 J/cm² of UVA plus 0.12 J/cm² UVB. Three days after treatment, proliferation was measured using a Coulter counter, and standard methods.

It will be seen from the results shown in FIG. 8 that the BSA-B6 complexes were very effective in inhibiting the proliferation of the keratinocytes.

EXAMPLE 6

The data set forth in examples 1-5, supra, deal with molecules which enhance cellular destruction. Such is not always desirable, however, and in this example and those which follow, experiments are set forth which describe molecules which inhibit this process. These molecules will be referred to as quenchers of photoexcited states, or "QPES" hereafter. Such compounds are characterized by an ability to inactivate the photoexcited state of a molecule which would then provoke the type of cell death described supra.

The proposed mechanism by which these molecules function is set forth in FIG. 9, although it is to be noted that applicants do not wish to be bound by this proposed mechanism. In brief, UV irradiation of a molecule leads to excitation of electrons (excited states, as "S*" in the figure), together with formation of excited singlets, and, after intersystem crossing (ISC), triplet states. These are key intermediates in the photodamage of cells. QPES compounds nullify this effect by accepting the excitation energy of the compounds associated with photodamage by energy transfer ("ET"), neutralizing phototoxic intermediates which relax back to ground state, dissipating the energy via harmless vibrational energy, or heat. The QPES compounds themselves are not depleted in this process, and neutralize multiple photodamaging molecules.

EXAMPLE 7

It is well known that ΦX174 plasmid is cleaved only by combined action of irradiation from solar simulated light, and AGE-pigment enriched protein, which acts as a UV sensitizer. AGE-BSA ("advanced glycation end product" modified bovine serum albumin), is a model for accumulation of endogenous skin sensitizers of the type described supra. Details of the assay showing this will be found in Wondrak, et al., Photochem. Photobiol. Sci. 1:355-363 (2002) incorporated by reference in its entirety. This assay was used in this example.

Plasmid cleavage was visualized by running samples on 1% agarose gels, and damage, i.e., formation of relaxed, open circular forms from closed circular forms (undamaged) were quantified via densitometry, which permitted assessment of the protective effect of a compound.

AGE-cleavage proceeds in the absence of oxygen, and cannot be suppressed fully via antioxidants. As such, if a compound suppresses plasmid cleavage it cannot be simply considered an antioxidant. In contrast, inhibition via quenching of the excited state, as described supra, must be presumed.

The results are presented in the Table which follows. Cytotoxic NaN$_3$, which is known as a quencher of photoexcited states, was effective, as were thiol compounds including glutathione ("GSH"), D-penicillamine, and N-acetyl-L-cysteine ("NAC").

This assay proves the principle discussed in example 7.

TABLE 1

Suppression of AGE-Sensitized DNA cleavage

| Compound | % Inhibition (±SD) |
|---|---|
| Catalase [400 u/mL] | 57.5 ± 4.7 |
| SOD [300 u/mL] | 48.0 ± 1.1 |
| Mannitol [20 mM] | 47.5 ± 2.5 |
| L-Histidine [20 mM] | 43.7 ± 0.4 |
| NaN$_3$ [20 mM] | 94.0 ± 0.5 |
| DABCO [20 mM] | 32.9 ± 1.1 |
| DFO [1 mM] | 51.3 ± 1.0 |
| D-Penicillamine [20 mM] | 95.7 ± 0.7 |
| NAC [20 mM] | 99.4 ± 0.9 |
| GSH [20 mM] | 100.0 ± 0.0 |

Figure 11:
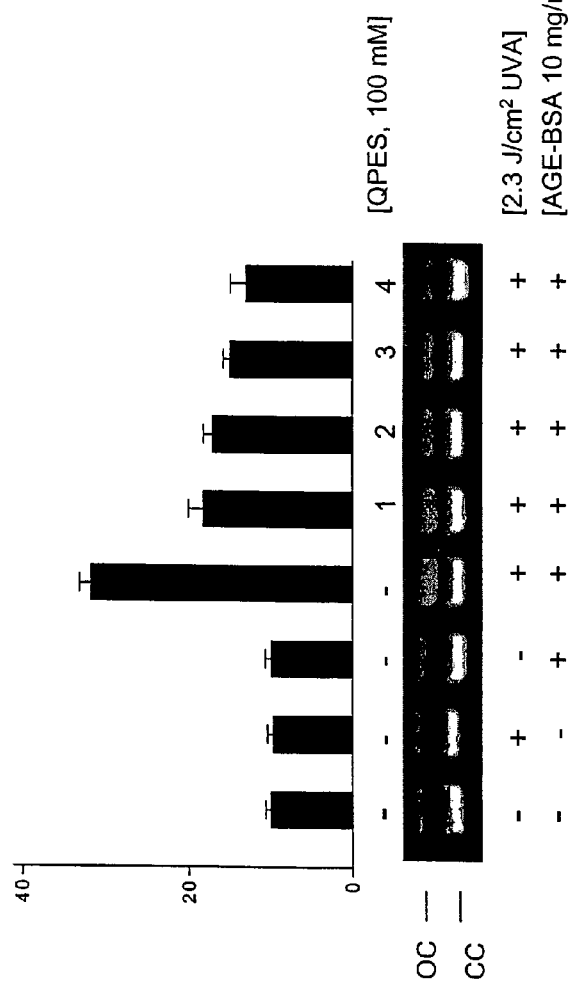
FIG. 11 depicts results from assays designed to show the efficacy of the proline derivatives in quenching photosensitized, DNA damage.

Using this assay, a series of proline related compounds and proline were tested. The structures of the compounds are set forth at FIG. 10. FIG. 11, sets forth the results of these experiments. The test compound was added, at 100 mM, and the plasmids were contacted with one, both, or neither of UVA light (2.3 J/cm$^2$), and AGE-BSA (10 mg/ml).

L-Pro-OCH$_3$ was the most potent of the quenchers, but all were effective.

EXAMPLE 8

As was discussed, supra, photoexcited oxygen, i.e., singlet oxygen, or "$^1O_2$", which is a spin paired homologue of ground state, triplet oxygen or "$^3O_2$," is the most important excited state molecule known to be in involved in phototoxicity. The involvement of singlet oxygen in photooxidative damage to, inter alia, cellular DNA, membrane lipids, and structural proteins like keratin and collagen, has been well documented. An assay was developed to determine the efficacy of compounds, such as proline and the proline derivatives described supra, in quenching singlet oxygen. See Lion, et al., Nature 263:442-443 (1976), incorporated by reference in its entirety.

It is well known that toluidine blue ("TB"), upon irradiation, generates $^1O_2$. In a known methodology, the $^1O_2$ is trapped via 2,2,6,6, tetramethylpiperidine, or "TEMP." A stable free radical, i.e., 2,2,6,6 tetramethylpiperdine-1-oxyl, or "TEMPO" forms, which can then be measured as a determination of $^1O_2$ generation. Key to this assay is the fact that other reactive oxygen species do not react with TEMP to produce TEMPO, thus ensuring that the assay is specific for formation of $^1O_2$.

TEMP, TB, and one of the molecules described supra were combined, and irradiated with visible light for 5 minutes, receiving a total dose of 36 J/cm$^2$. To elaborate, 100 µM TB, 7 mM TEMP, and 20 mM test compound were combined, in phosphate buffered saline, in a quarz capillary tube of 100 µl volume (1.5×90 mm), TEMPO free radical signal was measured via electron paramagnetic resonance using a commercially available apparatus. Controls were also run, to determine signal in the absence of test compound but in the presence of light, and the standard TEMPO resonance signal.

Figure 12:
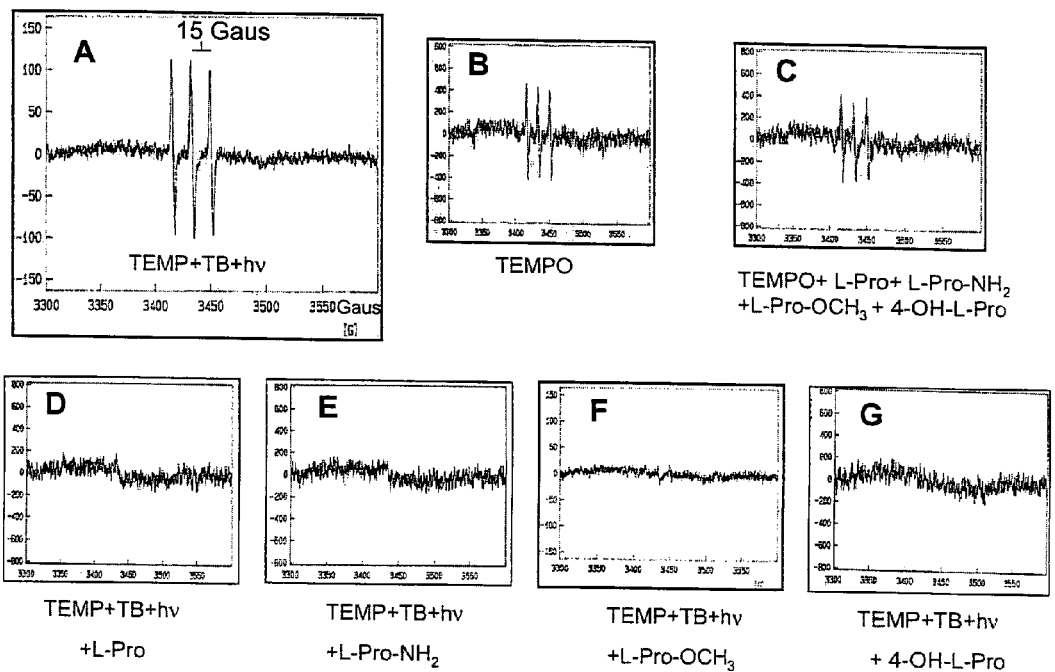
FIG. 12 shows how it was determined that compounds described herein quenched singlet oxygen.

The results, presented in FIG. 12, panels A-G, provide data as follows. Panel A shows the complete singlet oxygen generating system with production of the TEMPO signal. Panel B shows the spin signal of a commercial TEMPO reference. Panel C demonstrates that the effects observed in panels D-G were not caused by direct reaction of test compounds with TEMPO. Panels D & G demonstrate singlet oxygen quenching by proline derivatives and prove that derivatization of the carboxy group of proline or 4-hydroxylation does not impact quenching activity. Further, it shows that all of the compounds were effective quenchers.

In order to show that the quenching molecules were physical quenchers and were not consumed in the reaction, amino acid content of a mixture of TB and L-Pro in PBS was measured before and after a prolonged exposure to visible light (36 J/cm$^2$), using standard reversed phase HPLC methods for amino acid analysis. No changes were observed in the peak, retention time, or AUC values, indicating chemical inertness toward the $^1O_2$, providing evidence of physical quenching, rather than reactant consumption.

EXAMPLE 9

These experiments were designed to determine if the compounds proven to be quenchers were efficacious in protecting skin cells.

Cultured skin fibroblasts (CF3 cells) were exposed to photooxidative stress from $^1O_2$ which had formed, in situ, by dye sensitization.

In brief, 50,000 fibroblasts were seeded in a 35 mm culture dish, and then treated one day later with visible light (90 seconds exposure, providing 10.8 J/cm$^2$) in the presence or absence of TB (3.3 µM in Hanks buffered salt solution). Five minutes after treatment, cells were washed, with phosphate buffered saline. Test compound (10 mM) was present or absent in the culture during the radiation. After 3 days of cultivation, cells were harvested via trypsinization, and counted using a Coulter counter.

Figure 13:
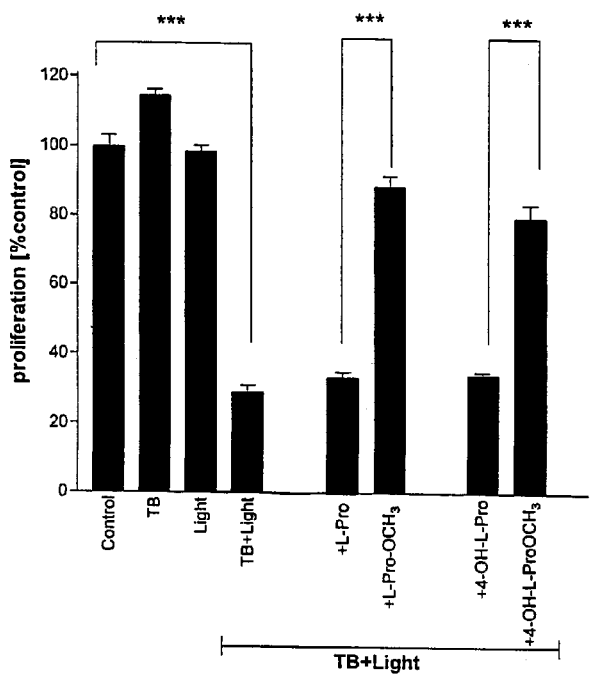
FIG. 13 shows the protective effect of various quencher molecules which inhibit skin cell photodamage.

The results indicated that cell proliferation was highly suppressed (70%) by the combination of TB and light, but either of these alone did not do so. The compounds L-Pro-OCH$_3$ and 4-OH-L-Pro-OCH$_3$ showed a very clear protective effect, as is shown in FIG. 13 and quantified in the table which follows:

| Cell Protection against Sensitized Photodamage [% ± SD, n = 3] | | |
|---|---|---|
| QPES - compound: | L-Pro | 6.2 ± 5.4 |
| | L-Pro-OCH$_3$ | 83.8 ± 10.9 |
| | 4-OH-L-Pro | 7.3 ± 2.5 |
| | 4-OH-L-Pro-OCH$_3$ | 71.0 ± 13.4 |

Protection was determined via the formula:

$$\text{protection (\%)} = \left[ \frac{\begin{array}{c}\% \text{ proliferation} ((TB + \text{Light} + QPES) - \\ \% \text{ proliferation} (TB + \text{Light})\end{array}}{\% \text{ proliferation (Control)} - \% \text{ proliferation} (TB + \text{Light})} \right] \times 100\%$$

The more active compounds in these experiments were the ester compounds. As is shown in FIG. 10, when the log P values of these compounds were determined, using methods well known in the art, the esters had significantly higher log P values than the non-esterified compounds. As the higher log P values are indicative of greater lipophilicity, it may be the case that their superior efficacy is due to maintaining longer residence time in skin and interaction with cell membranes. Proline ester derivatives with a log P value of from about −1.00 to about +8.00 are expected to be especially useful.

EXAMPLE 11

The compound 4-OH-L-proline methyl ester, described supra, is believed to be a new compound, representative of a new group of compounds. The synthesis, of the compound and guidelines for synthesis of other members of this family are now set forth.

4-hydroxy-L-proline was reacted with di-tert-butyl dicarbonate, in 1N NaOH at 5° C. for 30 minutes, followed by stirring, at room temperature, for an additional 3.5 hours.

The resulting protected 4-hydroxy proline was then reacted with dimethylformamide with potassium carbonate and methyl iodide, at 0° C., for 30 minutes, followed by stirring for an hour, at room temperature, to produce the methyl ester.

Deprotection of tert-butyl dicarbonate was then carried out using trifluoroacetic acid, and standard methods.

The key component in this reaction is methyl iodide. By varying the alkyl halide, esters containing alkyl groups with from 1-30, preferably 1-26 carbon atoms, can be obtained.

The foregoing examples set forth various aspects of the invention, which relate to methods for modulating photodamage, by administering at least one substance which modulates the effect of ultraviolet light on a subject. "Modulates" as used herein, refers generically to the ability to either increase the rate of photodamage, which is useful in situations where cellular proliferation needs to be arrested or to decrease the rate of damage. Examples of the former category include, e.g., psoriasis, acne, premalignant and malignant hyperproliferative disorders such as actinic keratosis, melanoma, non-melanoma skin cancer, breast cancer, and other cancers, as well as other conditions which will be known to the skilled artisan as involving the need to reduce cellular proliferation.

It is preferred that increase in photodamage, leading to a decrease in cellular proliferation, be accomplished via the use of at least one compound which has, as its "pharmacaphore" structure, a 3-hydroxypyridine ring, and is derived from a skin component, such as collagen. Exemplary of such compounds are 3-hydroxypyridine itself, vitamin B6, and most preferably, N-alkyl 3-hydroxypyridinium derivatives, such as salts, wherein the alkyl chain of the derivative comprises at least 2 and as many as 20 carbon atoms, in a preferably straight (but optimally branched) chain, which may or may not be substituted. More preferably, the alkyl group contains 2-10 carbon atoms in a straight chain, and most preferably, 2-5 carbon atoms. As was shown via the data set forth, supra, the N-ethyl derivative is especially preferred. Longer N-alkyl derivatives, which enhance the length of time the compound resides in the skin may be preferred in particular situations, such as, but not being limited to, situations where topical delivery of the compound is desired.

These molecules may be combined with, e.g., standard pharmaceutical ingredients and carriers, such as those employed in creams, lotions, shampoos, sprays, patches, or any of the known pharmacological delivery systems that are used for administering therapeutic agents to skin.

Where targeted therapy is especially desirable, the active ingredients may be attached to a second molecule which may be larger, to improve targeted delivery. Such larger molecules include, e.g., antibodies, ligands for receptors, hormones, and other molecules which either target and/or are taken up selectively by cells.

A further feature of the invention is the quenching feature of photodamage. As was shown, supra, proline and derivatives thereof are effective quenchers of photodamage. Especially efficacious are alkyl esters of proline, such as L-Pro-OCH$_3$ and 4-OH-L-proline; however, other compounds are useful, as has been shown. The modes of application are precisely as is described for the enhancers discussed, supra.

Other features of the invention will be clear to the skilled artisan, and need not be reiterated herein.

We claim:

1. A method for enhancing photodamage in a subject in need thereof, comprising applying to skin of said subject an amount of a photodamage modulator sufficient to enhance photodamage caused by ultraviolet light wherein said modulator is selected from the group consisting of a modulator which has a structure consisting of an N-alkyl-3-hydroxypyridine or salt thereof, wherein the alkyl moiety is 2-20 carbon atoms, vitamin B6, pyridinoline, and 3-hydroxypyridine.

2. The method of claim 1, wherein said modulator is collagen derived.

3. The method of claim 1, wherein said modulator is N-alkyl-3-hydroxypyridine or salt thereof.

4. The method of claim 1, wherein said alkyl moiety is an ethyl group.

5. The method of claim 1, wherein said modulator is connected to a carrier molecule.

6. The method of claim 1, wherein said modulator is vitamin B6, pyridinoline, or 3-hydroxypyridine.

7. The method of claim 1, comprising applying said modulator in the form of a cream, lotion, shampoo, spray or patch.

* * * * *